United States Patent [19]

Wright et al.

[11] Patent Number: 4,954,527

[45] Date of Patent: Sep. 4, 1990

[54] NOVEL POLYACETYLENE COMPOSITIONS AND THEIR METHODS OF USE

[75] Inventors: Amy E. Wright, Ft. Pierce; Winnie C. Thompson; May S. Lui, both of Vero Beach, all of Fla.

[73] Assignee: Harbor Branch Oceanographic Institution, Inc., Fort Pierce, Fla.

[21] Appl. No.: 131,233

[22] Filed: Dec. 7, 1987

Related U.S. Application Data

[63] Continuation of Ser. No. 879,071, Jun. 26, 1986, abandoned, which is a continuation-in-part of Ser. No. 825,060, Jan. 31, 1986, abandoned.

[51] Int. Cl.$^5$ ............... C07C 33/044; A61K 31/045; A61K 31/12; A61K 31/22

[52] U.S. Cl. ............... 514/675; 514/547; 514/738; 560/263; 568/412; 568/855; 568/856

[58] Field of Search ............... 514/547, 675, 738; 560/263; 568/412, 855, 856

[56] References Cited

FOREIGN PATENT DOCUMENTS 0642286 1/1979 U.S.S.R. ............... 568/856

OTHER PUBLICATIONS

Badanyan et al., "J. Chem. Soc." (1973) pp. 145–147.

*Primary Examiner*—J. E. Evans
*Attorney, Agent, or Firm*—Carroll F. Palmer

[57] ABSTRACT

This invention relates to novel polyacetylene compositions, a process of producing the compositions and a method for inhibiting tumors utilizing the compositions. More particularly, the compositions are antitumor polyacetylenes which are derived form marine organisms, i.e., the marine sponge *Cribrochalina dura*.

6 Claims, No Drawings

NOVEL POLYACETYLENE COMPOSITIONS AND THEIR METHODS OF USE

This application is a continuation of application Ser. No. 879,071 filed June 26, 1986, now abandoned, which in turn is a continuation-in-part of a application Ser. No. 825,060, filed Jan. 31, 1986, now abandoned.

FIELD OF THE INVENTION AND RELATED APPLICATION INFORMATION

This invention relates to new polyacetylene compositions which have useful antitumor activity. More particularly, this invention relates to new polyacetylene antitumor compositions derived from marine organisms, i.e., the marine sponge *Cribrochalina dura*.

BACKGROUND OF THE INVENTION

Various tumor related diseases inflict man. Considerable research has been devoted to oncology and antitumor measures. Tumors are common in a variety of mammals and the prevention, control of the growth and regression of tumors in mammals is important to man. The term tumor refers to abnormal masses of new tissue growth which is discordant with the economy of the tissue of origin or of the host's body as a whole.

Tumors inflict mammals and man with a variety of disorders and conditions including various forms of cancer and resultant cancerous cachexia. Cancerous cachexia refers to the symptomatic discomfort that accompanies the infliction of a mammal with a tumor. These symptoms include weakened condition of the inflicted mammal as evidenced by, for example, weight loss. The seriousness of cancer is well known, e.g., cancer is second only to heart and vascular diseases as a cause of death in man.

Considerable research and resources have been devoted to oncology and antitumor measures including chemotherapy. While certain methods and chemical compositions have been developed which aid in inhibiting, remitting or controlling the growth of tumors new methods and antitumor chemical compositions are needed.

Various polyacetylene compounds have been isolated from marine organisms. Certain of these compounds have been reported to have or potentially have cytotoxic activity. Compounds of interest are described in the following references:

D. Castiello, G. Cimino, S. De Rosa, S. De Stefano and G. Sodano. *Tetrahedron Letters*, 1980, 21, 5047-5050; G. Cimino, A. De Giuio, S. De Rosa, S. De Stefano and G. Sodano. *J. Nat. Prod.* 1985, 48, 22-27; G. Cimino, A. Crispino, S. De Rosa, S. De Stefano and G. Sodano. *Experientia*, 1981, 37, 924-926; and N. Fusetani, Y. Kato, S. Matsunaga and K. Hashimoto. *Tetrahedron Letters*, 1983, 24, 2771-2774.

It has now been found that certain novel polyacetylene compounds derived from extracts of the marine sponge, *Cribrochalina dura*, possess useful antitumor activity. One such composition named duryne has been isolated. This composition is reported in a paper entitled, "Duryne, A New Cytotoxic Agent From The Marine Sponge *Cribrochalina Dura*," presented at the Gordon Conference at the Scripps Institute in San Diego, Calif. on Feb. 2-7, 1986 by Amy E. Wright, Oliver J. McConnell, Shigeo Kohmoto, May S. Lui and Winnie C. Thompson. The entire disclosure of this presentation is incorporated herein by reference.

SUMMARY OF THE INVENTION

It is therefore an object of the invention to provide novel compositions which are useful as antitumor agents and a process for producing such novel antitumor compositions.

Additional objects and advantages of the invention will be set forth, in part, in the description which follows and in part will be obvious from this description, or may be learned by the practice of the invention. The objects and advantages of the invention are realized and obtained by means of the compositions, processes, methods, and the combinations particularly pointed out in the appended claims.

To achieve the objects in accordance with the purposes of the invention, as embodied and fully described here, the invention comprises compositions of the general formulae (I-III)

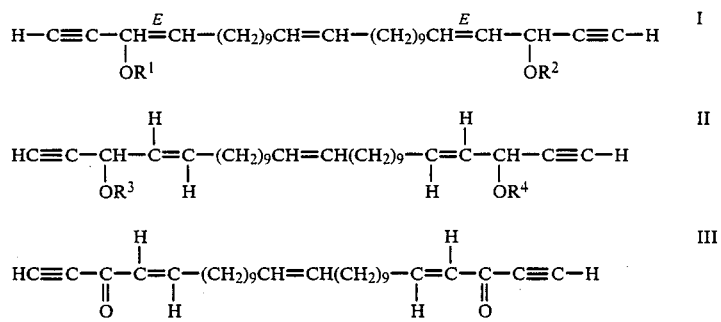

wherein $R^1$ and $R^2$ are the same or different and are selected from the group consisting of halogen, lower acyl, lower alkyl and hydrogen; $R^3$ and $R^4$ are the same or different and are selected from the group consisting of hydroxy, lower acyl and lower alkyl.

In preferred embodiments of the invention, the composition is substantially pure and $R^1$ or $R^2$ or both are hydrogen, $R^3$ or $R^4$ is a lower acyl or alkyl group which has from 1 to 4 carbon atoms. In more preferred embodiments of the invention, the invention comprises compositions of the formulae (I-V):

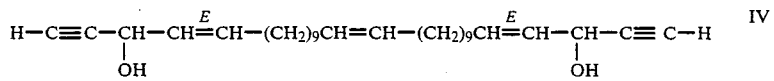

-continued

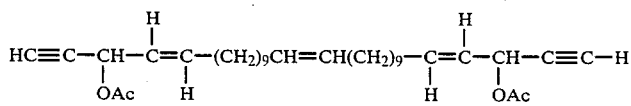

V

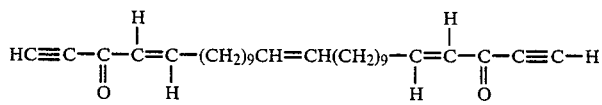

III

As embodied and fully described herein, the invention also comprises an antitumor composition comprising, as active ingredient, an effective antitumor amount of one or more compositions according to formulae I-V and a non-toxic pharmaceutically acceptable carrier or diluent.

As embodied and fully described herein, the invention also comprises a process to produce the compounds of formulae I-V. The process comprises the steps of collecting marine sponge *Cribrochalina dura;* contacting the sponge with a suitable organic solvent; obtaining an extract thereof; and isolating a compound according to formulae I from the extract.

In preferred embodiments of the invention the suitable organic solvent is selected from the group consisting of ethyl acetate, acetone, isopropanol, chloroform, ethylene chloride, methylene chloride, hexane, isooctane, toluene, benzene, butanol, n-propanol, methyl ethyl ketone, methanol, ethanol, and methyl isobutyl ketone.

As embodied and fully described herein, the invention further comprises a method for inhibiting tumors in a host and a therapeutic method for treating cancerous cachexia comprising contacting a tumor with an effective antitumor amount of one or more compositions of formulae I-VI.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention novel compositions are provided to achieve the objects in accordance with the purposes of the invention, as embodied and fully described herein, the invention comprises compositions of the general formulae (I-III):

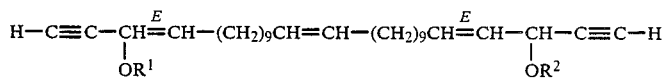

I

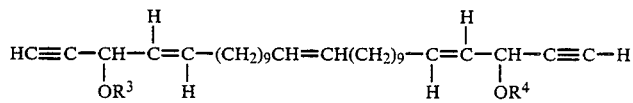

II

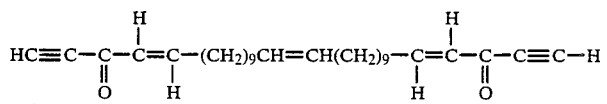

III wherein $R^1$ and $R^2$ are the same or different and are selected from the group consisting of halogen, lower acyl, lower alkyl and, hydrogen; $R^3$ and $R^4$ are the same or different and are selected from the group consisting of hydroxy, lower acyl and lower alkyl.

In preferred embodiments of the invention, the composition is substantially pure and $R^1$ or $R^2$ or both are hydrogen, $R^3$ or $R^4$ is a lower acyl or alkyl group having from 1 to 4 carbon atoms. In more preferred embodiments of the invention, the invention comprises compositions of the formula I:

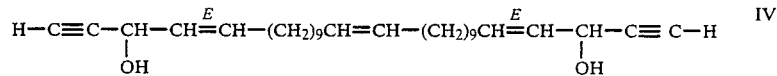

IV

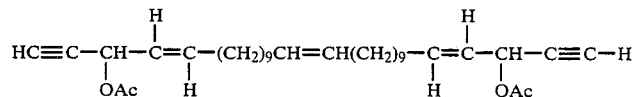

V

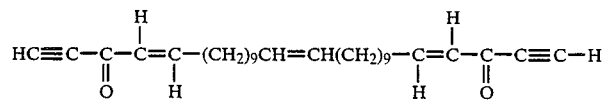

VI

In accordance with the invention, an antitumor composition is provided comprising as active ingredient an effective antitumor amount of one or more of the compositions described above and identified by formulae I–VI in a non-toxic pharmaceutically acceptable carrier or diluent. While effective amounts may vary, as conditions in which the antitumor compositions are used vary, a minimal dosage required for activity is generally between 0.01 and 100 micrograms against $10^5$ tumor cells. Useful examples of non-toxic pharmaceutically acceptable carriers or diluents include, but are not limited to, the following: ethanol, dimethyl sulfoxide and glycerol.

In accordance with the invention, a method for inhibiting tumors in a host is provided comprising contacting a tumor with an antitumor amount of one or more compositions according to formulae I–V. The effectiveness of the compositions of the invention for inhibiting tumors indicates their usefulness for controlling tumors in hosts including mammals and for treating cancerous cachexia.

In accordance with the invention, a process to produce compositions according to formula I comprises the steps of: collecting marine sponge *Cribrochalina dura;* contacting the sponge with a suitable organic solvent; obtaining an extract of the solvent and sponge mixture; and isolating a compound according to formula I.

The following is a detailed description and explanation of a preferred embodiment of the process of the invention to produce the compositions according to formula I. Marine sponge *Cribrochaline dura* is collected at a depth of 12 meters off Staniel Cay in the Bahamas. The sponge is admixed with ethyl acetate, homogenized and filtered to form a crude green oily extract. The extract is subjected to gross separation utilizing chromotography techniques. Compositions according to the invention are then isolated by various chromatographic techniques from the fractions obtained.

While ethyl acetate is the presently preferred choices for the solvent, other suitable solvents may be substituted. A suitable solvent should be capable of extracting a compound according to any one of formula I from other components of the marine sponge. Suitable solvents which may be substituted for ethyl acetate include, but are not limited to, the following organic solvents: acetone; isopropanol; chloroform; ethylene chloride; methylene chloride; hexane; isooctane; toluene; benzene; butanol; n-propanol; methyl ethyl ketone; methanol; ethanol; and methyl isobutyl ketone. Various solvent mixtures and ratios thereof may also be used in the invention as would be known to those skilled in the art.

Any suitable fractionation and isolation techniques may be utilized in accordance with the process of the invention. Suitable fractionation techniques include various chromatography techniques such as, high pressure liquid chromatography (HPLC) with a suitable column as would be known to those skilled in the art (e.g., a Whatman partisil column (M9 50/10) eluted with a suitable solvent such as, for example, 4:1 to 2:1, heptanes: ethyl acetate.

EXAMPLES

The invention will now be illustrated by examples. The examples are not intended to be limiting of the scope of the present invention. In conjunction with the detailed and general description above, the examples provide further understanding of the present invention and outline a process for producing compositions of the invention.

The following examples represent preferred embodiments of the compositions, processes and methods of the invention for satisfying the stated objects of the invention. The starting materials and reagents in the examples whose source or method of preparation are not indicated are commercially available from sources known to the art such as chemical supply houses

Example 1

Preparation of:

Composition 1 (Duryne)

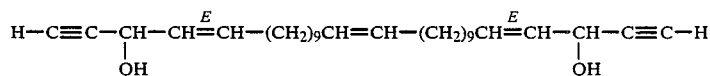

$$H-C\equiv C-CH(OH)-CH\overset{E}{=}CH-(CH_2)_9CH=CH-(CH_2)_9CH\overset{E}{=}CH-CH(OH)-C\equiv C-H$$

Marine sponge *Cribrochalina dura* was collected by SCUBA at a depth of 12 meters off Staniel Cay in the Bahamas. The sponge was frozen immediately after collection for transport to the laboratory. One hundred and fifteen grams of the frozen sponge was homogenized in a blender with ethyl acetate, the extract filtered and concentrated to yield a crude green oil (770 mg, 0.66% of wet weight). Vacuum flash chromatography using a step gradient of ethyl acetate-heptane as the eluent and Kieselgel 60-H as the stationary phase, followed by HPLC of the combined active fractions on a Whatman M-9 Partisil-10 $\mu$ column with isopropanol-heptane as the eluent (1:19) yielded 318 mg of duryne as a microcrystalline solid (m.p. 44°–45° C.). Duryne exhibits an RF of 0.5 (Kieselgel 60 $F_{2\ 5\ 4}$) on thin layer plates (EMScience) eluted with ETOAC-heptane (1:1). Table 1 demonstrates a gross separation of an extract which yields duryne.

TABLE 1

Gross separation of the extract of *Cribrochalina dura.*

| Fr. # | Elution Volume (ml) | Solvent Proportions | Yield mg |
|---|---|---|---|
| 1 | 100 | 100% Heptane | 23.7 |
| 2 | 50 | 5% EtOAc-95% heptane | 14.4 |
| 3 | 50 | 10% EtOAc-90% heptane | 5.4 |
| 4 | 50 | 20% EtOAc-80% heptane | 14.5 |
| 5 | 50 | 30% EtOAc-70% heptane | 59.8 |
| 6 | 50 | 40% EtOAC-60% heptane | 180.5 |
| 7 | 50 | 50% EtOAc-50% heptane | 65.1 |
| 8 | 50 | 60% EtOAc-40% heptane | 9.7 |
| 9 | 50 | 70% EtOAc-30% heptane | 6.1 |
| 10 | 50 | 80% EtOAc-20% heptane | 9.7 |
| 11 | 75 | 100% EtOAc | 6.9 |

HPLC separation of fractions 5 and 6 yielded duryne as a colorless solid. The separation was carried out on a Whatman M-9 Partisil Si -10 u column with 5% isopropanol-95% heptane as the eluent at a flow rate of 3.0 ml/min. Duryne was detected by both uv ($\lambda=230$ nm) and differential refractive index detection.

Duryne: LRMS:441, 423, 405, 393, 327.

UV:λMeOH=224(ε=313) and 230 (ε=307). IR: (CCl₄) cm⁻¹, 3600, 3300, 2910, 2840, 1450, 1350, 1080, 1000, 960, 650, 630.

¹H NMR (CDCl₃δ: 1.25 (28H, m); 2.0 (4H, m); 2.08 (4H, m); 2.54 (2H, d J=4.84 (2H, bdd J=6.0, 1.0 Hz); 5.34 (2H, m); 5.59 2H, ddt J=15.1, 6.2, 1.4 Hz); 5.92 (2H, ddt J=15.1, 1.1, 6.8 Hz). ¹C NMR (CDCl₃): 27.2 (2C t); 28.8 (2C t) 29.1 (2C t); 29.4 (2C t); 29.5 (4C t); 29.7 (2C t); 29.9 (2C t); 31.9 (2C t); 62.7 (2C d); 73.9 (2C d); 83.6 (2C s); 128.3 (2C d); 129.9 (2C d); 134.5 (2C d).

Example 2

Composition 2

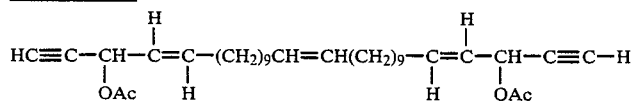

Composition 2 (acetate) is prepared by acetylating duryne by Synthesis techniques known to those skilled in the art. For example, treating of duryne with acetic anhydride in the presence of pyridine.

Example 3

Composition 3

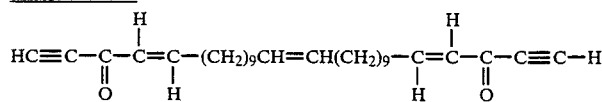

Composition 3 (ketone) is prepared by oxidation of duryne by Synthesis techniques known to those skilled in the art. For example, treating duryne with a solution of manganese dioxide in methylene chloride.

ANTITUMOR ACTIVITIES OF THE COMPOUNDS OF THE INVENTION

The following assay methods were utilized to illustrate the antitumor effectiveness of the composition of Formula IV corresponding to composition 1 of the examples.

P388 MOUSE LEUKEMIA CELL ASSAY

Maintenance of Cell Line

P388 mouse leukemia cells are grown in Dulbecco MEM medium with 10% horse serum, 4mM glutamine, and 20ug/ml gentamycin (Biologos, Inc.). Cells are incubated in 10% $CO_2$ and subcultured 2 times per week.

PROCEDURE

1. Add compound to each well of a 24-well plate or tube and allow solvent to evaporate to dryness.
2. Add 2ml (1.2×10⁵) cells to each well or tube and mix.
3. Incubate in 10% $CO_2$ at 35° for 48 hours.
4. Read plates with an inverted microscope, scoring activity from 1+ to 4+ as follows: ND (not detectable), 90%; 1+, 75–90%; 2+, 50–74%; 3+, 25–49; 4+, 25% of control growth. Cell counts are performed on each tube and results are reported as percent of control.

HUMAN TUMOR CELL LINE ASSAY

Maintenance of Cell Lines HCT-8 human colon tumor cells are grown in RPM1 1640 medium (Biologos, Inc). All media are supplemented with 10% fetal bovine serum and contain 50ug/ml gentamycin. All human tumor cell lines are incubated in 5% $CO_2$ at 37° and subcultured once a week.

PROCEDURE

1. Seed 1ml cell (5000 HCT-8, 8000 A549, 12000 MCF-7) in each well of a 24-well plate.
2. Incubate in a $CO_2$-incubator for 48 hours.
3. Add compound to each well and incubate for an additional 120 hours.
4. Discard medium and stain with methylene blue (HCT-8) or crystal violet (A549 and MCF-7).
5. Compare cell density of drug-treated well with that of the control (no drug added) as follows: ND (not detectable), 90%; 1+, 75–90%; 2+, 50–74%; 3+, 25–49%; 4+, 25% of control growth.

The results of the assays carried out according to the above protocol are summarized below in Table 2. Compounds of formulae IV/l are cytotoxic in vitro against P388 murine leukemia cells; L-1210 murine leukemia cells; A549 human lung cells; HCT-8 human colon cells; and MCF-7 human breast cells.

TABLE 2

| Compound Formula/ Example | Antitumor Assay Results | | | |
|---|---|---|---|---|
| | Concentration | P388 | A549 | HCT-8 | MCF-7 |
| IV/1 (duryne) | 1 ug/ml | N.A. | 4+ | 4+ | 4+ |
| | 0.5 | 4+ | N.A. | N.A. | N.A. |
| | 0.4 | 4+ | N.A. | N.A. | N.A. |
| | 0.3 | 4+ | N.A. | N.A. | N.A. |
| | 0.2 | 4+ | N.A. | N.A. | N.A. |
| | 0.1 | 4+ | 4+ | 4+ | 1+ |
| | 0.05 | N.D. | N.A. | N.A. | N.A. |
| | 0.01 | N.A. | N.D. | N.D. | N.D. |

N.D. = not detected
N.A. = data not available

This data shows that for concentrations of duryne of 0.1 mg/ml and higher growth of all of the tumor cells was inhibited to less than 25% (except for MCF-7 wherein 1ug ml inhibited growth to less than 25%). It is apparent from the preceding antitumor assay data that the compositions of the invention are effective for inhibiting or destroying tumor cells and tumors and therefore controlling diseases caused by or related to such tumors in fulfillment of the objects of the invention.

The scope of the present invention is not limited by the description, examples, and suggested uses herein and modifications can be made without departing from the spirit of the invention. For example, it may be noted that other derivatives of the compounds of examples 1–3 such as a halogenated derivative may possess antitumor activity analogous to those preferred embodiments described above. Further, the compositions described herein may have other useful applications such as, for example, analgesic applications. Application of the compositions of the present invention can be accomplished by any suitable therapeutic method and technique as is presently or prospectively known to those skilled in the art. Thus, it is intended that the present invention cover the modifications and variations of this invention provided that they come within the scope of the appended claims and their equivalents.

What is claimed is:

1. A substantially pure compound of the formulae:

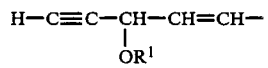

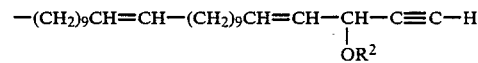

or

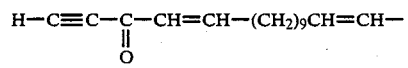

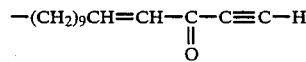

wherein $R^1$ and $R^2$ are the same or different and are selected from the group consisting of lower acyl and hydrogen.

2. A compound of claim 1 according to the formula:

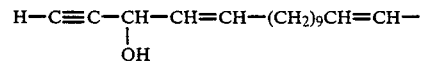

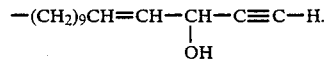

3. A compound of claim 1 according to the formula:

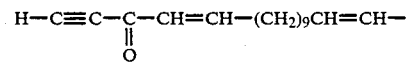

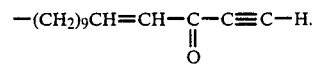

4. A pharmaceutical composition comprising as an active ingredient a pharmaceutically effective amount of a substantially pure compound according to the formulae:

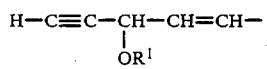

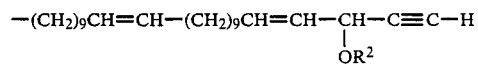

or

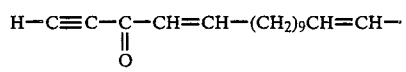

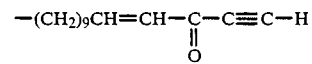

wherein $R^1$ and $R^2$ are the same or different and are selected from the group consisting of lower acyl and hydrogen and a non-toxic, pharmaceutically acceptable carrier or diluent.

5. A composition of claim 4 comprising the compound according to the formula:

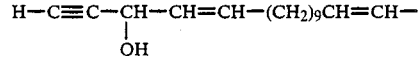

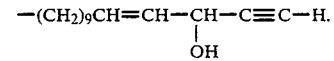

6. A pharmaceutical composition comprising as an active ingredient a pharmaceutically effective amount of a substantially pure compound according to the formula:

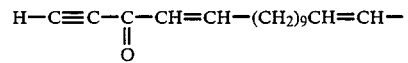

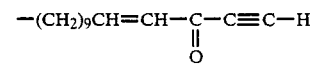

and a non-toxic, pharmaceutically acceptable carrier or diluent.

* * * * *